United States Patent
Gliner et al.

(10) Patent No.: US 7,620,456 B2
(45) Date of Patent: *Nov. 17, 2009

(54) SYSTEMS AND METHODS FOR REDUCING THE LIKELIHOOD OF INDUCING COLLATERAL NEURAL ACTIVITY DURING NEURAL STIMULATION THRESHOLD TEST PROCEDURES

(75) Inventors: Bradford Evan Gliner, Sammamish, WA (US); Kent Leyde, Redmond, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 355 days.

This patent is subject to a terminal disclaimer.

(21) Appl. No.: 11/388,190

(22) Filed: Mar. 23, 2006

(65) Prior Publication Data

US 2007/0043392 A1 Feb. 22, 2007

Related U.S. Application Data

(63) Continuation of application No. 10/350,947, filed on Jan. 24, 2003, now Pat. No. 7,024,247, which is a continuation-in-part of application No. 09/978,134, filed on Oct. 15, 2001, now Pat. No. 7,305,268, which is a continuation-in-part of application No. 09/802,808, filed on Mar. 8, 2001, now Pat. No. 7,010,351.

(60) Provisional application No. 60/217,981, filed on Jul. 13, 2000.

(51) Int. Cl.
*A61N 1/00* (2006.01)

(52) U.S. Cl. .......................................... 607/45

(58) Field of Classification Search .................... 607/2, 607/45, 46, 48, 57, 63, 68–73; 600/544, 600/545; 606/129

See application file for complete search history.

(56) References Cited

U.S. PATENT DOCUMENTS 2,721,316 A 10/1955 Shaw (Continued)

FOREIGN PATENT DOCUMENTS

DE 19750043 5/1999

(Continued)

OTHER PUBLICATIONS

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

(Continued)

*Primary Examiner*—George Manuel
(74) *Attorney, Agent, or Firm*—Melissa Acosta; Peter Lando; Christopher S. L. Crawford

(57) ABSTRACT

Test procedures for determining a neural stimulation threshold of a patient. In one embodiment, the procedure includes applying a test stimulation signal to the patient and monitoring the patient for a response to the test stimulation signal. The procedure can further include determining a first neural stimulation threshold and calculating a second neural stimulation threshold. The first neural stimulation threshold corresponds to the lowest intensity test stimulation signal that evokes a patient response. The second neural stimulation threshold corresponds to a treatment stimulation signal directed toward affecting a neural activity within the patient.

59 Claims, 4 Drawing Sheets

U.S. PATENT DOCUMENTS

| | | |
|---|---|---|
| 3,628,193 A | 12/1971 | Collins |
| 3,650,276 A | 3/1972 | Burghele et al. |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Arseneault et al. |
| 4,328,813 A | 5/1982 | Ray |
| 4,340,038 A | 7/1982 | McKean |
| 4,431,000 A | 2/1984 | Butler et al. |
| 4,474,186 A | 10/1984 | Ledley et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,054,906 A | 10/1991 | Lyons, Jr. |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,215,086 A | 6/1993 | Terry, Jr. et al. |
| 5,224,491 A | 7/1993 | Mehra |
| 5,255,678 A | 10/1993 | Deslauriers et al. |
| 5,263,967 A | 11/1993 | Lyons, III et al. |
| 5,271,417 A | 12/1993 | Swanson et al. |
| 5,282,468 A | 2/1994 | Klepinski |
| 5,299,569 A | 4/1994 | Wernicke et al. |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,736 A | 7/1996 | Haimovich et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther |
| 5,601,611 A | 2/1997 | Fayram et al. |
| 5,611,350 A | 3/1997 | John |
| 5,628,317 A | 5/1997 | Starkebaum et al. |
| 5,674,251 A | 10/1997 | Combs et al. |
| 5,676,655 A | 10/1997 | Howard, III et al. |
| 5,683,422 A | 11/1997 | Rise |
| 5,702,429 A | 12/1997 | King |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski et al. |
| 5,735,814 A | 4/1998 | Elsberry et al. |
| 5,750,376 A | 5/1998 | Weiss et al. |
| 5,752,979 A | 5/1998 | Benabid |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,709 A | 11/1998 | Rise et al. |
| 5,843,148 A | 12/1998 | Gijsbers et al. |
| 5,843,150 A | 12/1998 | Dreessen et al. |
| 5,865,842 A | 2/1999 | Knuth et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,026,326 A | 2/2000 | Bardy |
| 6,035,236 A | 3/2000 | Jarding et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,537 A | 10/2000 | Rise |
| 6,128,538 A | 10/2000 | Fischell et al. |
| 6,134,474 A | 10/2000 | Fischell et al. |
| 6,152,143 A | 11/2000 | Edwards |
| 6,161,044 A | 12/2000 | Silverstone |
| 6,161,045 A | 12/2000 | Fischell et al. |
| 6,176,242 B1 | 1/2001 | Rise |
| 6,198,958 B1 | 3/2001 | Ives et al. |
| 6,205,360 B1 * | 3/2001 | Carter et al. .................. 607/57 |
| 6,210,417 B1 | 4/2001 | Baudino et al. |
| 6,221,908 B1 | 4/2001 | Kilgard et al. |
| 6,230,049 B1 | 5/2001 | Fischell et al. |
| 6,236,892 B1 | 5/2001 | Feler |
| 6,246,912 B1 | 6/2001 | Sluijter et al. |
| 6,280,462 B1 | 8/2001 | Hauser et al. |
| 6,301,493 B1 | 10/2001 | Marro et al. |
| 6,319,241 B1 | 11/2001 | King et al. |
| 6,339,725 B1 | 1/2002 | Naritoku et al. |
| 6,353,754 B1 | 3/2002 | Fischell et al. |
| 6,354,299 B1 | 3/2002 | Fischell et al. |
| 6,356,792 B1 | 3/2002 | Errico |
| 6,360,122 B1 | 3/2002 | Fischell et al. |
| 6,366,813 B1 | 4/2002 | DiLorenzo |
| 6,375,666 B1 | 4/2002 | Mische |

| | | |
|---|---|---|
| 6,405,079 B1 | 6/2002 | Ansarinia |
| 6,418,344 B1 | 7/2002 | Rezai et al. |
| 6,427,086 B1 | 7/2002 | Fischell et al. |
| 6,456,886 B1 | 9/2002 | Howard, III et al. |
| 6,459,936 B2 | 10/2002 | Fischell et al. |
| 6,463,328 B1 | 10/2002 | John |
| 6,464,356 B1 | 10/2002 | Sabel |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,484,059 B2 | 11/2002 | Gielen |
| 6,487,450 B1 | 11/2002 | Chen |
| 6,499,488 B1 | 12/2002 | Hunter et al. |
| 6,505,075 B1 | 1/2003 | Weiner |
| 6,507,755 B1 | 1/2003 | Gozani et al. |
| 6,556,868 B2 | 4/2003 | Naritoku et al. |
| 6,597,954 B1 | 7/2003 | Fischell et al. |
| 6,615,065 B1 | 9/2003 | Barrett et al. |
| 6,622,048 B1 | 9/2003 | Mann et al. |
| 6,633,780 B1 | 10/2003 | Berger |
| 6,665,562 B2 | 12/2003 | Gluckman et al. |
| 6,687,525 B2 | 2/2004 | Llinas et al. |
| 6,690,974 B2 | 2/2004 | Archer et al. |
| 6,708,064 B2 | 3/2004 | Rezai |
| 6,725,094 B2 | 4/2004 | Saberski |
| 6,764,498 B2 | 7/2004 | Mische |
| 6,782,292 B2 | 8/2004 | Whitehurst |
| 6,795,737 B2 | 9/2004 | Gielen et al. |
| 6,810,286 B2 | 10/2004 | Donovan et al. |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,907,296 B1 | 6/2005 | Doan et al. |
| 6,934,580 B1 | 8/2005 | Osorio et al. |
| 6,944,497 B2 | 9/2005 | Stypulkowski |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,110,820 B2 | 9/2006 | Tcheng et al. |
| 2002/0077670 A1 | 6/2002 | Archer |
| 2002/0087201 A1 | 7/2002 | Firlik |
| 2002/0091419 A1 | 7/2002 | Firlik et al. |
| 2002/0099412 A1 | 7/2002 | Fischell |
| 2002/0169485 A1 | 11/2002 | Pless et al. |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0114886 A1 | 6/2003 | Gluckman et al. |
| 2003/0125772 A1 | 7/2003 | Olson et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | DeCharms |
| 2004/0102828 A1 | 5/2004 | Lowry et al. |
| 2004/0111127 A1 | 6/2004 | Gliner et al. |
| 2004/0131998 A1 | 7/2004 | Marom et al. |
| 2004/0138550 A1 | 7/2004 | Hartlep et al. |
| 2004/0158298 A1 | 8/2004 | Gliner |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2006/0015153 A1 | 1/2006 | Gliner et al. |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |

FOREIGN PATENT DOCUMENTS

| | | |
|---|---|---|
| EP | 0 319 844 | 6/1989 |
| EP | 1 145 736 | 4/1994 |
| EP | 0 998 958 | 10/2000 |
| EP | 1 180 056 | 11/2003 |
| WO | WO 87/07511 | 12/1987 |
| WO | WO-94/07564 | 4/1994 |
| WO | WO-95/21591 | 8/1995 |
| WO | WO-98/06342 | 2/1998 |
| WO | WO-01/97906 | 12/2001 |
| WO | WO-02/09811 | 2/2002 |
| WO | WO-02/36003 | 5/2002 |
| WO | WO-02/38031 | 5/2002 |
| WO | WO-02/38217 | 5/2002 |
| WO | WO-03/082402 | 3/2003 |
| WO | WO-03/043690 | 5/2003 |

OTHER PUBLICATIONS

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Behrens, T. et al., "Non-invasive mapping of connections between human thalamus and cortex using diffusion imaging," Nature Neuroscience, vol. 6 No. 7, pp. 750-757 (Jul. 2003).

Bel, S. and Bauer, B.L., "Dorsal Column Stimulation (DCS): Cost to Benefit Analysis," Acta Neurochirurgica, Suppl. 52, pp. 121-123 (1991).

Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].

Bluestone, Avraham Y. et al., "Three-dimensional optical tomography of hemodynamics in the human head," Optics Express, vol. 9, No. 6, pp. 272-286 (Sep. 10, 2001).

Brain Electrical Stimulation to Enhance Recovery After Stroke. ClinicalTrials.gov. [Retrieved on Dec. 22, 2005]. Retrieved from the internet <URL http://www.clinicaltrials.gov/ct/show/NCT00085657?order=2>.

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).

Bury, Scott et al., "The Effects of Behavioral Demand on Motor Cortical and Cerebellar Structural Plasticity After Brain Injury in Adult Rats," [Retrieved on Mar. 1, 2003]. Retrieved from the internet: <URL: http://www.mcmaster.ca.inabis98/schallert/bury0827/index.html>.

Butefisch et al., "Mechanisms of use-dependent plasticity in the human motor cortex," Proc. Natl. Acad. Sci. USA, vol. 97, No. 7, pp. 3661-3665 (Mar. 2000).

Canavero, S. and Paolotti, R., "Extradural Motor Cortex Stimulation for Advanced Parkinson's Disease: Case Report," Movement Disorders 15(1): 160-171, 2000.

Cao, Yue et al., "Cortical Language Activation in Stroke Patients Recovering From Aphasia With Functional MRI," Stroke, vol. 30, pp. 2331-2340, Nov. 1999.

Cheun et al., "Differentiation of a Stem Cell Line Toward a Neuronal Phenotype," Int. J. Devl. Neuroscience, vol. 9, No. 4, pp. 391-404 (1991).

Cincotta et al., "Reorganization of the motor cortex in a patient with congenital hemiparesis and mirror movements," Neurology, vol. 55, pp. 129-131 (2000).

Classen, et al., "Rapid Plasticity of Human Cortical Movement Representation Induced by Practice," The Journal of Neurophysiology, vol. 79, No. 2, pp. 1117-1123 (Feb. 1998).

Cohen et al., "Studies of Neuroplasticity With Transcranial Magnetic Stimulation," The Journal of Clinical Neurophysiology, vol. 15, No. 4 (1998).

Cramer, S.C. and Bastings, E.P., "Mapping clinically relevant plasticity after stroke," Neuropharmacology vol. 19, No. 5, pp. 842-851 (Apr. 2000).

Cytokines Web Clinical Significance. Cytokines Web, 2 pages. [Retrieved on Sep. 2, 2005]. Retrieved from the internet: <URL: <http://cmbi.bjmu.edu.cn/cmbidata/cgf/CGF_Database/cytweb/roles/index.html>>.

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

De Ridder, Dirk et al., "Magnetic and electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppresses specific excitatory circuits in the human motor cortex," Physiology in Press; published online on Apr. 21, 2005 as 10.1113/jphysio.2005.087288.

Ding, Yuemin et al., "Neural Plasticity After Spinal Cord Injury," Current Pharmaceutical Design vol. 11, No. 11, pp. 1441-1450, Abstract Only- 1 page (Apr. 2005).

Duncan, Pamela W. et al., "Defining post-stroke recovery: implications for design and interpretation of drug trials," Neuropharmacology vol. 39, pp. 835-841 (2000).

Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93:873-875 (2000).

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371-377 (1990).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Haglund, Michael M. et al., "Optical imaging of epileptiform and functional activity in human cerebral cortex," Nature, vol. 358, pp. 668-671, (Aug. 20, 1992).

Hayakawa, Toshiji et al., "Changes in Cerebral Oxygenation and Hemodynamics During Obstructive Sleep Apneas," Chest, vol. 109, pp. 916-921 (1996).

Hodge, Jr., C.J. and Boakye, M., "Biological Plasticity: The Future of Science in Neurosurgery," Neurosurgery, vol. 48, No. 1 (Jan. 2001).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., 1 page [Retrieved on Oct. 14, 2005]. Retrieved from the internet: <URL http://www.iss.com/Products/imagent_fmri.html>.

Huang, Ying-Zu et al., "Theta Burst Stimulation of the Human Motor Cortex," Neuron, vol. 45, pp. 201-206 (Jan. 20, 2005).

Hummel, Friedhelm et al., "Effects of non-invasive cortical stimulation on skilled motor function in chronic stroke," Brain Advance Access, Jan. 5, 2005, pp. 1-10, Brain.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent™.pdf>.

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kauhanen et al., "Domains and Determinants of Quality of Life After Stroke Caused by Brian Infarction," Arch. Phys. Med. Rehabil., vol. 81, pp. 1541-1546 (Dec. 2000).

Keyvani, Kathy et al., "Suppression of proteasome C2 contralateral to ischemic lesions in rat brain," Brain Research, vol. 858, pp. 386-392, 2000.

Kilgard, Michael et al., "Cortical Map Reorganization Enabled by Nucleus Basalis Activity,"Science, vol. 279 pp. 1714-1717 (Mar. 13, 1998).

Kopell et al., "The Continuing Evolution of Psychiatric Neurosurgery," CNS Spectrums, vol. 5, No. 10, pp. 20-31 (Oct. 2000).

Lang, N. et al., "Preconditioning with Transcranial Direct Current Stimulation Sensitizes the Motor Cortex to Rapid-Rate Transcranial Magnetic Stimulation and Controls the Direction of After-Effects," Biological Psychiatry, 56:634-639 (2004).

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias. BioChemistry of PD. [Retrieved on Dec. 22, 2005]. Retrieved from the internet <URL http://www.mayo.edu/fdp/pd-info/dyskinesias.htm>.

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G., et al., "A sham stimulation-controlled trial of rTMS of the unaffected hemisphere in stroke patients," Neurology, vol. 64, pp. 1802-1804 (2005).

Martin et al, "Transcranial Magnetic Stimulation as a Complementary Treatment for Aphasia," Semin Speech Language, vol. 25, pp. 181-191 (2004) Abstract Only- 1 page.

Martinez et al., "Motor hand recovery after stroke Prognostic yield of early transcranial magnetic stimulation," Electromyography. Clin. Neurophysiology, vol. 39, pp. 405-410 (1999).

Meyerson, B.A. et al., "Motor Cortex Stimulation as Treatment of Trigeminal Neuropathic Pain", Acta Neurochirurgica Supplementum, vol. 58, pp. 150-153 (1993).

Netz et al., "Reorganization of motor output in the non-affected hemisphere after stroke,"Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al., "Level of action of cathodal DC polarisation induced inhibition of the human motor cortex," Dec. 2, 2002, Clinical Neurophysiology 114 (2003) 600-604.

Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Nudo, Randolph J., et al., "Recovery after damage to motor cortical areas," Current Opinion in Neurobiology, vol. 9, Issue 6, pp. 740-747, Dec. 1, 1999.

Oliveri et al., "Paired transcranial magnetic stimulation protocols reveal a pattern of inhibition and facilitation in the human parietal cortex," The Journal of Physiology, 529.2, pp. 461-468 (2000).

Panchanathan, Sethuraman et al., "Rehabilitation of patients with hemispatial neglect using visual-haptic feedback in Virtual reality environment," [Retrieved on Dec. 22, 2005]. Retrieved from the Internet <URL <http://www.public.asu.edu/~tmcdani/publications.htm>>.

Pascual-Leone et al., "Study and Modulation of Human Cortical Excitability With Transcranial Magnetic Stimulation," Journal of Clinical Neurophysiology, vol. 15, No. 4 (1998).

Pascual-Leone et al., "Transcranial magnetic stimulation and neuroplasticity,"Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimuation," Neuron, vol. 45, pp. 181-183 (Jan. 20, 2005).

Penn, Michael, "Stemming Parkinson's," On Wisconsin Alumni Magazine, Summer 2003, [Retrieved on Dec. 22, 2005]. Retrieved from the internet <URL http://www.uwalumni.com/onwisconsin/2003_summer/research.html>.

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annual Review of Neuroscience 23:393-415 (2000).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

SCIRun. Scientific Computing and Imaging Institute, 2 pages. [Retrieved on Jul. 24, 2005]. Retrieved from the internet: <URL: <http://software.sci.utah.edu/scirun.html>>.

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Stefan et al., "Introduction of plasticity in the human motor cortex by paired associative stimulation," Brian, vol. 123, No. 3, pp. 575-584 (Mar. 2000).

Strangman, Gary et al., "A Quantitative Comparison of Simultaneous Bold fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topography," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

The INVOS Cerebral Oximeter. Somanetics, 1 page [Retrieved on Dec. 22, 2005]. Retrieved from the internet <URL <http://www.somanetics.net/invos.htm>>.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 26, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography. Absolute Astronomy Reference, 2 pages. [Retrieved on Jul. 24, 2005]. Retrieved from the internet: <URL: http://www.absoluteastronomy.com/encyclopedia/T/Tr/Tractography.htm>.

Tsubokawa, T. et al., "Chronic Motor Cortex Stimulation for the Treatement of Central Pain", Acta Neurochirurgica Supplementum, vol. 52, pp. 137-139 (1991).

Tsubokawa, T. et al., "Treatment of Thalamic Pain by Chronic Motor Cortex Stimulation", PACE, vol. 14, pp. 131-134 (Jan. 1991).

Tsubokawa, T., "Chronic Motor Cortex Stimulation in Patients with Thalamic Pain," J. Neurosurg 78:393-401, (Mar. 1993).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Van Der Lee et al., "The Intra- and Interrater Reliability of the Action Research Arm Test: A Practical Test of Upper Extremity Function in Patients With Stroke," Arch. Phys. Med Rehabil., vol. 82, pp. 14-19 (Jan. 2001).

Walker-Batson et al., "Amphetamine Paired With Physical Therapy Accelerates Motor Recovery After Stroke," Stroke, vol. 26, No. 12, pp. 2254-2259 (1995).

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischemic Nerve Block," The Journal of Neuroscience, vol. 18, No. 3, pp. 1115-1123 (Feb. 1998).

* cited by examiner

SYSTEMS AND METHODS FOR REDUCING THE LIKELIHOOD OF INDUCING COLLATERAL NEURAL ACTIVITY DURING NEURAL STIMULATION THRESHOLD TEST PROCEDURES

CROSS-REFERENCE TO RELATED APPLICATION(S)

This application is a continuation of U.S. application Ser. No. 10/350,947, filed Jan. 24, 2003, now U.S. Pat. No. 7,024,247 which is a Continuation-in-Part of U.S. application Ser. No. 09/978,134, filed Oct. 15, 2001, now U.S. Pat. No. 7,305,268 which is a Continuation-in-Part of U.S. application Ser. No. 09/802,808, filed Mar. 8, 2001, now U.S. Pat. No. 7,010,351 which claims priority to U.S. Provisional Application No. 60/217,981, filed Jul. 13, 2000, all of which are incorporated herein by reference in their entireties.

TECHNICAL FIELD

The present disclosure is related to systems and methods for reducing the likelihood of inducing collateral neural activity while determining threshold parameters for electrically stimulating a region in the cortex or other area of the brain.

BACKGROUND

A wide variety of mental and physical processes are controlled or influenced by neural activity in particular regions of the brain. The neural-functions in some areas of the brain (i.e., the sensory or motor cortices) are organized according to physical or cognitive functions. There are also several other areas of the brain that appear to have distinct functions in most individuals. In the majority of people, for example, the areas of the occipital lobes relate to vision, the regions of the left interior frontal lobes relate to language, and the regions of the cerebral cortex appear to be consistently involved with conscious awareness, memory, and intellect.

Many problems or abnormalities with body functions can be caused by damage, disease and/or disorders in the brain. Effectively treating such abnormalities may be very difficult. For example, a stroke is a very common condition that damages the brain. Strokes are generally caused by emboli (e.g., obstruction of a vessel), hemorrhages (e.g., rupture of a vessel), or thrombi (e.g., clotting) in the vascular system of a specific region of the brain, which in turn generally cause a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus an adjunctive therapy such as amphetamine treatment. For most patients, however, such treatments are minimally effective and little can be done to improve the function of an affected body part beyond the recovery that occurs naturally without intervention.

Neural activity is governed by electrical impulses or "action potentials" generated in and propagated by neurons. While in a quiescent state, a neuron is negatively polarized and exhibits a resting membrane potential that is typically between −70 and −60 mV. Through chemical connections known as synapses, any given neuron receives from other neurons excitatory and inhibitory input signals or stimuli. A neuron integrates the excitatory and inhibitory input signals it receives, and generates or fires a series of action potentials when the integration exceeds a threshold potential. A neural firing threshold may be, for example, approximately −55 mV. Action potentials propagate to the neuron's synapses, where they are conveyed to other neurons to which the neuron is synaptically connected.

The neural activity in the brain can be accordingly influenced by electrical energy that is supplied from a man-made source such as a waveform generator. Various neural functions can thus be promoted or disrupted by applying an electrical current to the cortex or other region of the brain. As a result, researchers have attempted to treat damage, disease and disorders in the brain using electrical or magnetic stimulation signals to control or affect brain functions. One treatment approach, transcranial electrical stimulation (TES), involves placing an electrode on the exterior of the scalp and delivering an electrical current to the brain through the scalp and skull. Another treatment approach, transcranial magnetic stimulation (TMS), involves producing a high-powered magnetic field adjacent to the exterior of the scalp over an area of the cortex. Yet another treatment approach involves direct electrical stimulation of neural tissue using implanted electrodes.

A neural stimulation signal may comprise a series or train of electrical or magnetic pulses that can affect neurons within a target neural population, and may be defined or described in accordance with stimulation signal parameters including pulse amplitude, pulse frequency, duty cycle, stimulation signal duration, and/or other parameters. Electrical or magnetic stimulation signals applied to a population of neurons can depolarize neurons within the population toward their threshold potentials. Depending upon stimulation signal parameters, this depolarization can cause neurons to generate or fire action potentials. Neural stimulation that elicits or induces action potentials in a functionally significant proportion of the neural population to which the stimulation is applied is referred to as supra-threshold stimulation; neural stimulation that fails to elicit action potentials in a functionally significant proportion of the neural population is defined as sub-threshold stimulation. In general, supra-threshold stimulation of a neural population triggers or activates one or more functions associated with the neural population, but sub-threshold stimulation by itself fails to trigger or activate such functions. Supra-threshold neural stimulation can induce various types of measurable or monitorable responses in a patient. For example, supra-threshold stimulation applied to a patient's motor cortex can induce muscle fiber contractions.

Although electrical or magnetic stimulation of neural tissue may be directed toward producing an intended type of therapeutic, rehabilitative, or restorative neural activity, such stimulation may result in collateral neural activity. In particular, neural stimulation delivered beyond a certain intensity, level, or amplitude can give rise to seizure activity and/or other types of collateral activity, which may be undesirable and/or inconvenient in a neural stimulation situation.

Seizure activity may originate at a seizure focus, which is a collection of neurons (e.g., on the order of 1000 neurons) exhibiting a characteristic type of synchronous firing activity. In particular, each neuron within a seizure focus exhibits a firing response known as a paroxysmal depolarizing shift (PDS). The PDS is a large magnitude, long duration depolarization that triggers a neuron to fire a train or burst of action potentials. Properly functioning feedback and/or feed-forward inhibitory signaling mechanisms cause an ensuing afterhyperpolarization, through which the neuron's membrane potential returns to a hyperpolarized state below its firing threshold. Following the afterhyperpolarization, the neuron may undergo another PDS.

The afterhyperpolarization limits the duration of the PDS, thereby helping to ensure that synchronous neural firing activity remains localized to the seizure focus. Inhibitory feedback signaling provided by neurons surrounding a seizure focus, commonly referred to as surround inhibition, is particularly important in constraining seizure activity to the seizure focus. In the event that inhibitory signaling mechanisms fail and/or are unable to overcome or counter PDS activity, neurons within the seizure focus recruit other neurons to which they are synaptically coupled into their synchronous firing pattern. As a result, synchronous firing activity spreads beyond the seizure focus to other areas of the brain. This can lead to a cascade effect in which seizure activity becomes increasingly widespread and accompanying clinical manifestations become increasingly significant.

In view of the foregoing, it may be very important in any given neural stimulation situation to determine an appropriate stimulation signal amplitude, level, or intensity. However, an appropriate stimulation signal level may vary on a per-patient basis and possibly over time for any particular patient. Notwithstanding, determination of a neural stimulation threshold corresponding to a minimum or near-minimum stimulation signal level that induces or generates a measurable or monitorable patient response can provide a reference point for establishing a stimulation signal intensity appropriate for a neural stimulation session.

Various types of neural stimulation thresholds exist. For example, an electromyography or electromyographic (EMG) threshold may be defined as a lowest or near-lowest level of neural stimulation that generates an EMG signal of a particular magnitude. An EMG signal provides a measurement of electrical discharges associated with the innervation of muscle fibers by one or more motor neurons, and the onset of muscle fiber contraction in response to such electrical discharges. As another example, a sensation threshold may be defined as a lowest or near-lowest level of neural stimulation at which a patient notices, perceives, or experiences a physical sensation such as a tingling or vibration in a muscle group or limb. As yet another example, a movement threshold may be defined as a lowest or near-lowest level of neural stimulation that induces a noticeable movement in a patient's limb.

Unfortunately, neural stimulation threshold testing can itself induce collateral neural activity. During a typical neural stimulation threshold test procedure, a very low amplitude test stimulation signal is initially applied to a patient. The amplitude of the test stimulation signal is then increased incrementally, while other test stimulation signal parameters (e.g., frequency, pulse characteristics, duty cycle, etc.) remain unchanged or unmodified. As its amplitude is increased, the test stimulation signal is delivered to the patient in an uninterrupted or continuous manner. A lowest or near-lowest test stimulation signal amplitude that evokes a given type of patient response is correspondingly defined as the neural stimulation threshold. The patient is subsequently treated using a stimulation signal having parameters identical to those of the test stimulation signal, with the possible exception of stimulation signal amplitude, which may be a predetermined value based on the neural stimulation threshold.

Stimulation signal characteristics and manners in which stimulation signals are applied to a target neural population can significantly affect the likelihood of inducing collateral neural activity. Conventional neural stimulation threshold test procedures fail to adequately address this consideration, and thus may be susceptible to inducing seizure activity and/or other types of collateral neural activity. Hence, there is a need for systems and methods that reduce the likelihood of inducing such activity during neural stimulation threshold testing.

DETAILED DESCRIPTION

Figure 1:
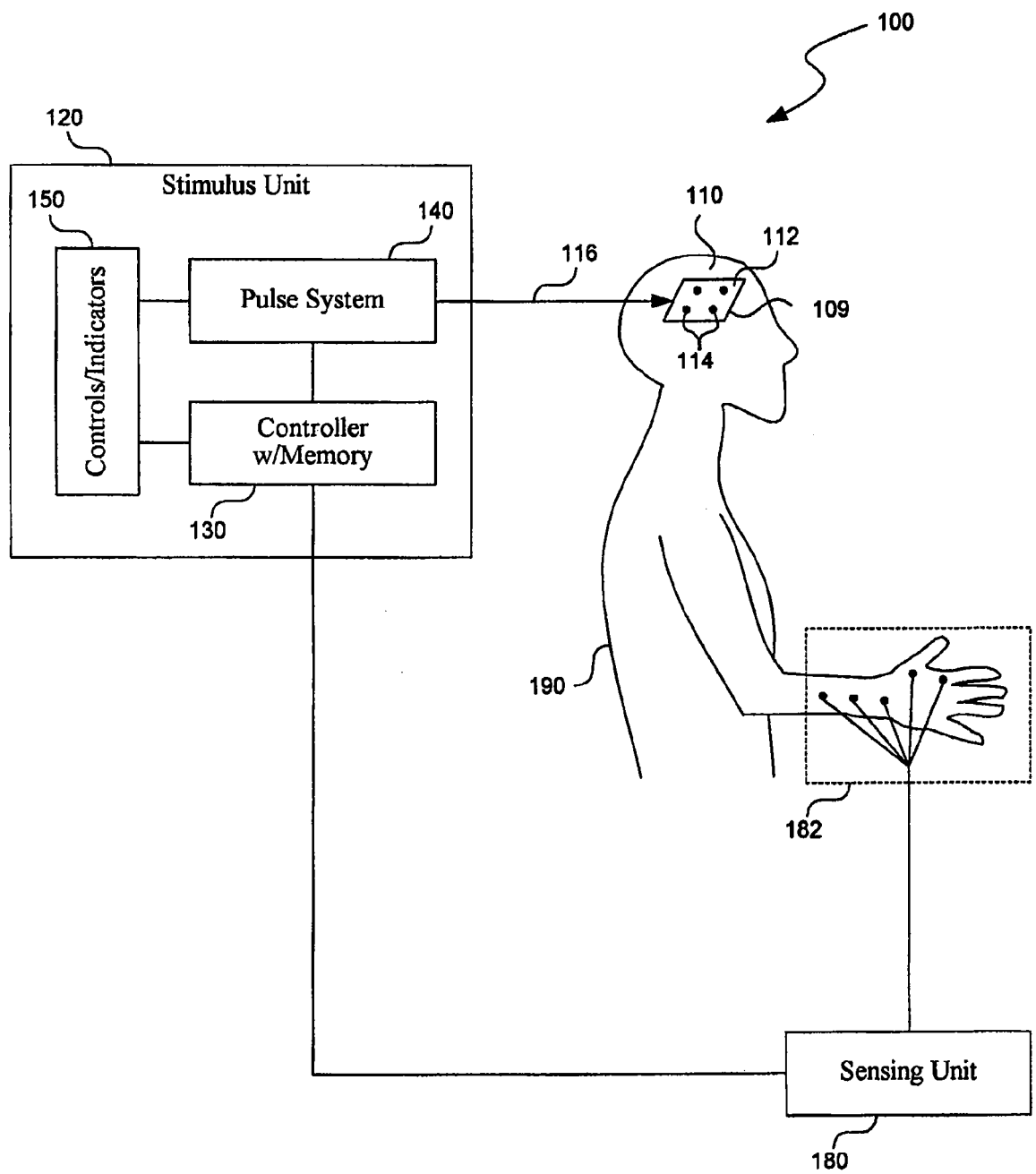
FIG. 1 is a schematic illustration of a system for neural stimulation threshold testing according to an embodiment of the invention.

The following disclosure describes systems and methods for reducing the likelihood of inducing collateral neural activity during the application of test stimulation signals to a patient for the purpose of determining a threshold stimulation level that induces or evokes a particular type of patient response, behavior, activity, sensation, perception, and/or reaction. In the context of the present invention, collateral neural activity may comprise seizure activity and/or essentially any other type of neural activity that may be undesirable, unwanted, unintended, and/or counterproductive relative to an intended or desired neural activity associated with neural stimulation threshold testing.

Various methods in accordance with the present invention are directed toward neural stimulation threshold test procedures that temporally manage the application of test stimulation signals to a patient. Neural stimulation lasting beyond several seconds (e.g., approximately 5 seconds) can lead to prolonged neural firing responses known as afterdischarges. Afterdischarges in a target neural population increase or tend to increase neural activity in the population, which may excite other neurons synaptically coupled to the target population. Afterdischarges can therefore increase the likelihood of inducing collateral neural activity. Neural stimulation threshold test procedures in accordance with the present invention may therefore apply limited duration test stimulation signals to patients.

Neural stimulation applied to a target neural population can affect the future excitability or firing likelihood of neurons in the target population. In particular, recently stimulated neurons may exhibit enhanced excitability in the presence of subsequent stimulation. A neural population that receives sub-threshold stimulation during a first time period may exhibit an increased firing susceptibility in the presence of same stimulation applied during a second time period when the second time period and the first time period are separated by only a brief interval (e.g., seconds or several seconds). Moreover, neural activity, such as afterdischarges, may persist for many milliseconds or seconds after a stimulation signal is interrupted or terminated. Hence, neural stimulation threshold test procedures in accordance with the present invention may additionally or alternatively provide for a quiescent time interval between successive threshold determination attempts during which test stimulation signals are not applied or delivered to the target neural population.

Various methods in accordance with the present invention may additionally or alternatively be directed toward neural stimulation threshold test procedures in which test stimulation signals and a treatment stimulation signal used to treat a patient may parametrically differ beyond their amplitudes. For example, depending upon stimulation signal parameters, neurons within a target population may respond to a stimulation signal in a synchronous manner. In particular, the ability of neurons to synchronously respond to or follow a stimulation signal is a function of the stimulation signal's frequency. Neurons can readily follow a stimulation signal up to a frequency of approximately 100 Hertz, but beyond this frequency their ability to follow the stimulation signal degrades. Supra-threshold stimulation delivered to a target neural population at a frequency that-neurons can readily follow may drive synchronous firing activity within the population. In view of the foregoing, a neural stimulation threshold test procedure in accordance with the present invention may measure a first neural stimulation threshold using one or more test stimulation signals having a first frequency; and subsequently calculate a second neural stimulation threshold corresponding to a treatment stimulation signal that may have a second frequency different from the first frequency. The calculation of the second neural stimulation threshold may be performed in accordance with one or more transformation equations, as described in detail below.

FIG. 1 is a schematic illustration of a system 100 for neural stimulation threshold testing according to an embodiment of the invention. In one embodiment, the system 100 comprises a stimulus unit 120 configured to deliver stimulation signals to a patient 190 through a patient interface 109. The system 100 may further include a sensing unit 180 coupled to the patient 190 and the stimulus unit 120.

The stimulus unit 120 is capable of generating and outputting stimulation signals, which comprise electrical and/or magnetic signals or stimuli. The stimulus unit 120 may perform, direct, and/or facilitate neural stimulation threshold test procedures in a manner that reduces the likelihood of inducing collateral neural activity in accordance with the present invention. Neural stimulation threshold test procedures may involve the application of one or more test stimulation signals to a patient 190 in manners described in detail below. The stimulus unit 120 may additionally perform, direct, and/or facilitate neural stimulation treatment procedures to treat a particular neurological condition and/or affect or influence a given type of neural activity. Neural stimulation treatment procedures involve the application of a treatment stimulation signal to a patient. The treatment stimulation signal, for example, is typically at a level or amplitude that corresponds to a result obtained during neural stimulation threshold test procedures (e.g., 20% to 80% of a neural stimulation threshold).

The stimulus unit 120 may comprise a controller 130, a pulse system 140, and a set of controls/indicators 150. The controller 130 may include a processor, a memory, and a programmable computer medium. The controller 130 may be implemented as a computer or microcontroller, where the programmable medium comprises software loaded into the memory, and/or hardware that performs, directs, and/or facilitates neural stimulation threshold test procedures in accordance with the methods of the present invention. The controls/indicators 150 can include a display device, an input/output device, and/or other types of devices for exchanging commands and/or output with a computer.

The pulse system 140 can generate energy pulses, and send such pulses to the patient interface 109. In one embodiment, the pulse system 140 forms a portion of a Transcranial Magnetic Stimulation (TMS) device through which externally applied magnetic stimulation signals create electrical currents in the patient's brain. In such an embodiment, the patient interface 109 may comprise an electromagnetic coil arrangement in a manner understood by those skilled in the art. In another embodiment, the pulse system 140 forms a portion of an electrical stimulation device; in this case the patient interface 109 may comprise an electrode array configured to deliver electrical stimulation signals to the patient 190 as described in detail hereafter.

The patient interface 109 shown in FIG. 1 comprises an electrode array 110 including a support member 112 and a plurality of electrodes 114 carried by the support member 112. The electrode array 110 is generally implanted into the patient 190 and configured for cortical stimulation, deep brain stimulation, and/or other types of neural stimulation. The electrode array 110 may comprise a cortical neural-stimulation device, such as a device described in U.S. application Ser. No. 09/802,808, incorporated herein by reference. The electrodes 114 may be coupled to the stimulus unit 120 by a link 116, which may be wire-based or wireless.

The electrode array 110 and the pulse system 140 can be integrated into a single implantable stimulation apparatus, as described in U.S. application Ser. No. 09/082,808. An integrated pulse system 140 and electrode array 110 may be configured for implantation into a patient's skull such that the electrodes 114 can contact the patient's dura matter or pia matter in a given cortical region. Such a device can have an internal power source that can be implanted into the patient 190, and/or an external power source coupled to the pulse system 140 via electromagnetic coupling or a direct connection. In alternate embodiments, the pulse system 140 is an external unit that is not implanted into the patient 190. An external pulse system 140 can provide stimuli to the electrodes 114 using RF energy, electromagnetism, or wire terminals exposed on the patient's scalp.

The sensing unit 180 may comprise a system or apparatus for measuring or monitoring one or more types of patient reactions evoked or induced in response to test stimulation signals applied during neural stimulation threshold test procedures. The sensing unit 180 can be coupled to the stimulus unit 120 by at least one link 186, which may be wire-based and/or wireless. The stimulus unit 120 may issue a signal over the link 186 to synchronize the application of test stimulation signals to the patient 190 with sensing unit measuring, monitoring, and/or recording operations. Depending upon embodiment details, the sensing unit 180 may also use the link 186 to communicate status information and/or measurement results to the stimulus unit 120.

In one embodiment, the sensing unit 180 comprises an EMG device coupled to a plurality of electrodes or leads 182. The EMG device may detect or monitor motor evoked potentials (MEPs) associated with muscle fiber innervation in a manner understood by those skilled in the art. An EMG threshold may be defined, for example, as a lowest or near-lowest level of neural stimulation that induces an MEP that departs from baseline electrical activity by an amplitude greater than 50 microvolts peak-to-peak under 1000× amplification and 20-1000 Hertz bandpass conditions. The electrodes 182 may comprise surface, percutaneous, and/or implanted probes, which may be positioned or configured to measure electrical activity associated with one or more muscles or muscle groups. In one embodiment, the electrodes 182 include a ground lead and bipolar surface leads configured to monitor MEPs in an interosseus muscle, a wrist extensor, a wrist flexor, and/or other muscles.

Various embodiments of the present invention may alternatively or additionally detect or determine other types neural stimulation thresholds, such as a sensation threshold, a movement threshold, an Electroencephalogram (EEG) threshold, a Magnetoencephalogram (MEG) threshold, and/or an imaging threshold. The structure and/or function of the sensing unit 180 may correspond to the type of neural stimulation threshold under consideration. For example, to facilitate detection of a movement threshold, the sensing unit 180 may comprise a set of motion detectors, accelerometers, and/or strain gauges configured to detect or monitor one or more types of patient movements. To detect or determine an EEG threshold, the sensing unit 180 may comprise an EEG system configured to monitor changes in a patient's EEG during neural stimulation threshold test procedures. Such an EEG system may include and/or utilize electrodes positioned upon the patient's scalp, and/or intracranially upon a brain surface or in a subcortical region.

To detect or determine an MEG threshold, the sensing unit 180 may comprise an MEG system configured to monitor variations in the patient's MEG in response to test stimulation signals. To measure or determine an imaging threshold, the sensing unit 180 may comprise a neural imaging system configured to monitor and image a patient's neural activity during neural stimulation threshold test procedures. Suitable neural imaging systems include Magnetic Resonance Imaging (MRI) systems, functional MRI (fMRI) systems, or Positron Emission Tomography (PET) systems.

Different types of neural stimulation thresholds may vary with respect to measurement or observation subjectivity, and/or sensitivity to stimulation signal intensity. In general, determination of an EMG threshold may be a less subjective process than determination of a movement threshold, which may be a less subjective process than determination of a sensation threshold. Also, an EMG threshold may be triggered or induced at a lower stimulation signal intensity than a sensation or a movement threshold. In general, a sensation threshold may be triggered or induced at a lower stimulation signal intensity than a movement threshold, although this need not always be the case. Determination of movement and/or sensation thresholds may involve or rely upon human perception and verbal and/or visual feedback, and may not require the use of a sensing unit 180.

Figure 2:
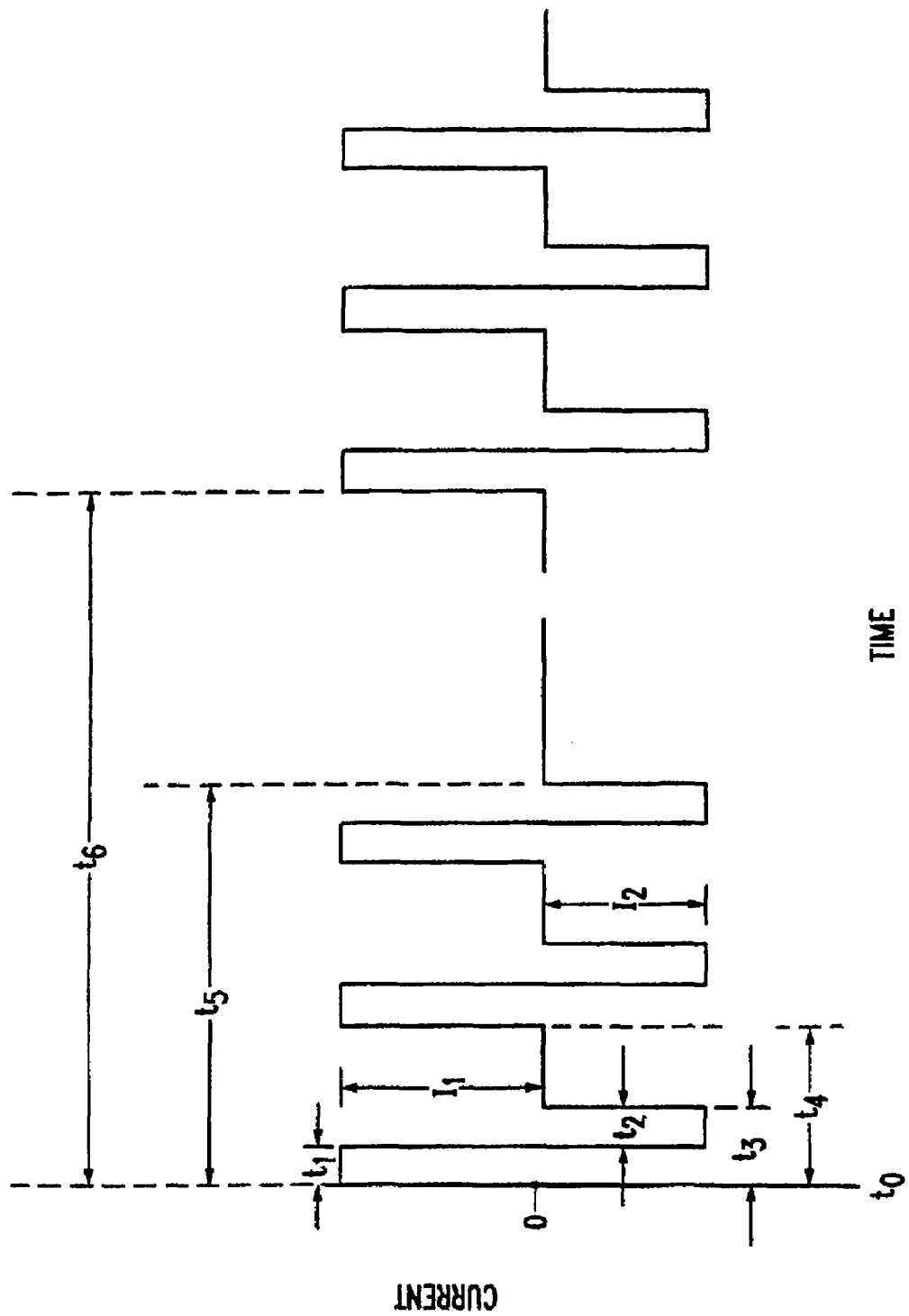
FIG. 2 is a graph illustrating several parameters that may describe or characterize a stimulation signal.

As previously indicated, the stimulus unit 120 is configured to deliver stimulation signals to a patient 190; the stimulation signals may comprise test stimulation signals and/or treatment stimulation signals. FIG. 2 is a graph illustrating several parameters that may define, describe, or characterize stimulation signals. A stimulus start time $t_0$ defines an initial point at which a stimulation signal is applied to the patient interface 110. In one embodiment, the stimulation signal may be a biphasic waveform comprising a series of biphasic pulses, and which may be defined, characterized, or described by parameters including a pulse width $t_1$ for a first pulse phase; a pulse width $t_2$ for a second pulse phase; and a pulse width $t_3$ for a single biphasic pulse. The parameters can also include a stimulus repetition rate $1/t_4$ corresponding to a pulse repetition frequency; a stimulus pulse duty cycle equal to $t_3$ divided by $t_4$; a stimulus burst time $t_5$ that defines a number of pulses in a pulse train; and/or a pulse train repetition rate $1/t_6$ that defines a stimulus burst frequency. Other parameters include a peak current intensity $I_1$ for the first pulse phase and a peak current intensity $I_2$ for the second pulse phase. Those skilled in the art will understand that pulse intensity or amplitude may decay during one or both pulse phases, and a pulse may be a charge-balanced waveform. Those skilled in the art will further understand that in an alternate embodiment, pulses can be monophasic or polyphasic.

Figure 3:
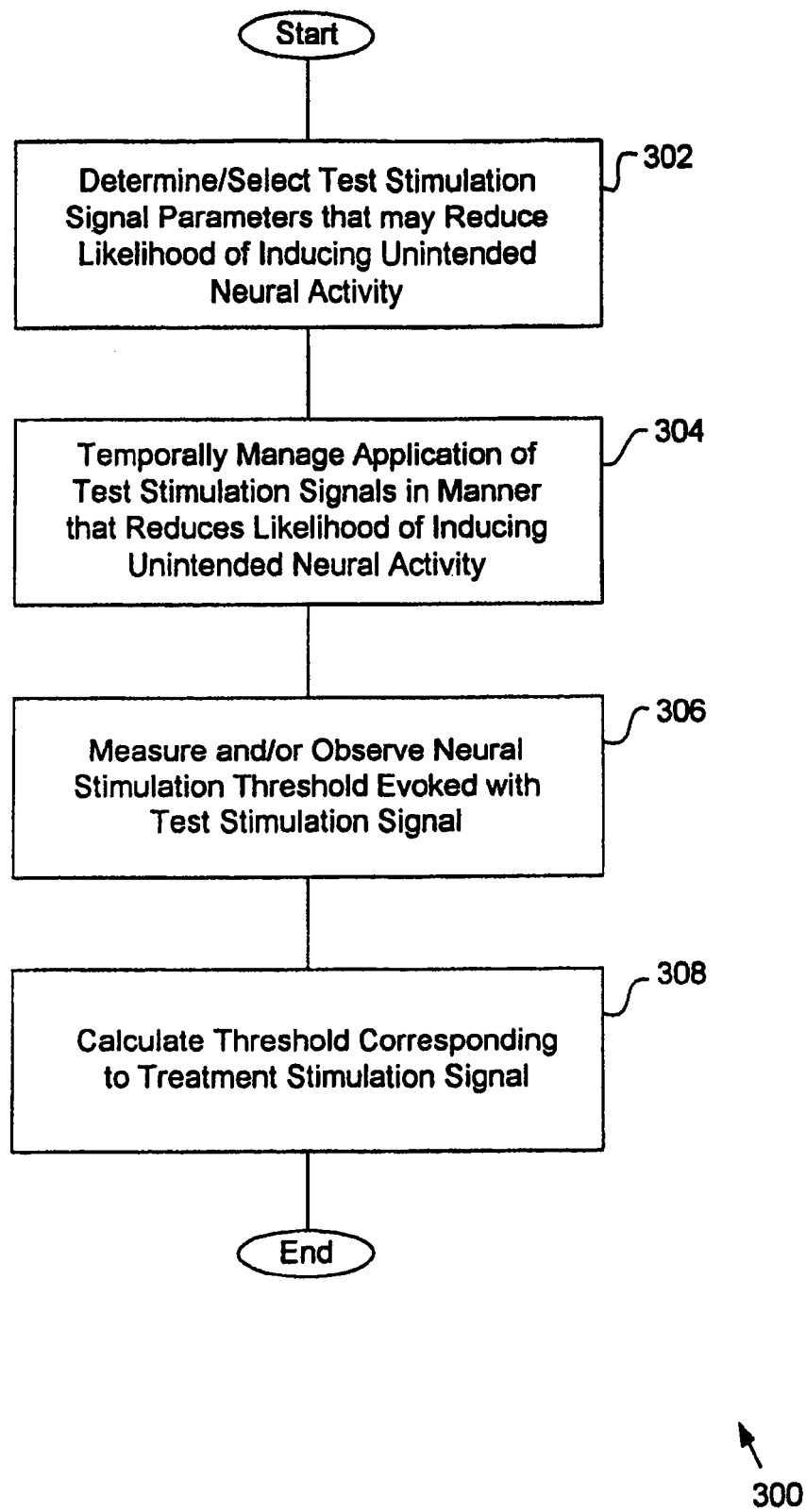
FIG. 3 is a flowchart illustrating various methods for neural stimulation threshold testing according to an embodiment of the invention.

FIG. 3 is a flowchart illustrating various methods for neural stimulation threshold testing according to an embodiment of the invention. In one embodiment, a method 300 may include a parameter determination procedure 302 involving determination, selection, or specification of test stimulation signal parameters that may reduce a likelihood of inducing collateral neural activity. Depending upon embodiment details, one or more types of test stimulation signal parameter sets, selections, and/or settings may be preprogrammed into the stimulus unit 120. A stimulus unit operator (e.g., a medical professional) may select a particular set of test stimulation signal parameters using the stimulus unit's controls/indicators 150. Exemplary test stimulation signal parameter selections that may reduce the likelihood of inducing collateral neural activity are described in detail below with reference to FIG. 4.

The method 300 may additionally include a signal management procedure 304 that involves managing the temporal application of test stimulation signals to a patient 190 in a manner that reduces the likelihood of inducing collateral neural activity. A stimulus unit operator may use the stimulus unit's controls/indicators 150 to initiate the signal management procedure 304. Particular manners of temporally managing test stimulation signal application in accordance with the present invention are described in detail below with reference to FIG. 4. The method 300 may additionally include an observation or measurement procedure 306 that involves observing and/or measuring one or more neural stimulation thresholds based upon one or more patient reactions and/or behaviors induced in response to the test stimulation signals. The observation procedure 306 may be performed using the sensing unit 180 and/or human perception and feedback.

The method 300 may further include a calculation procedure 308 involving calculation, mapping, and/or determination of a neural stimulation threshold corresponding to a treatment stimulation signal that is to be applied to the patient 190 for treating a neurological condition and/or affecting neural activity. The treatment stimulation may be parametrically distinct from one or more test stimulation signals with respect to one or more parameters. Operations performed and/or directed by the calculation procedure 308 may be based upon one or more measured and/or observed neural stimulation thresholds. The calculation procedure 308 may involve the use of one or more conversion or mapping functions and/or data tables stored in a memory of the stimulation unit. Such functions and/or data tables may be based upon known relationships and/or one or more empirical measurement histories capable of correlating test stimulation signal parameters with treatment stimulation signal parameters for a range of neural stimulation thresholds as measured or observed in association with the observation procedure 306.

Figure 4:
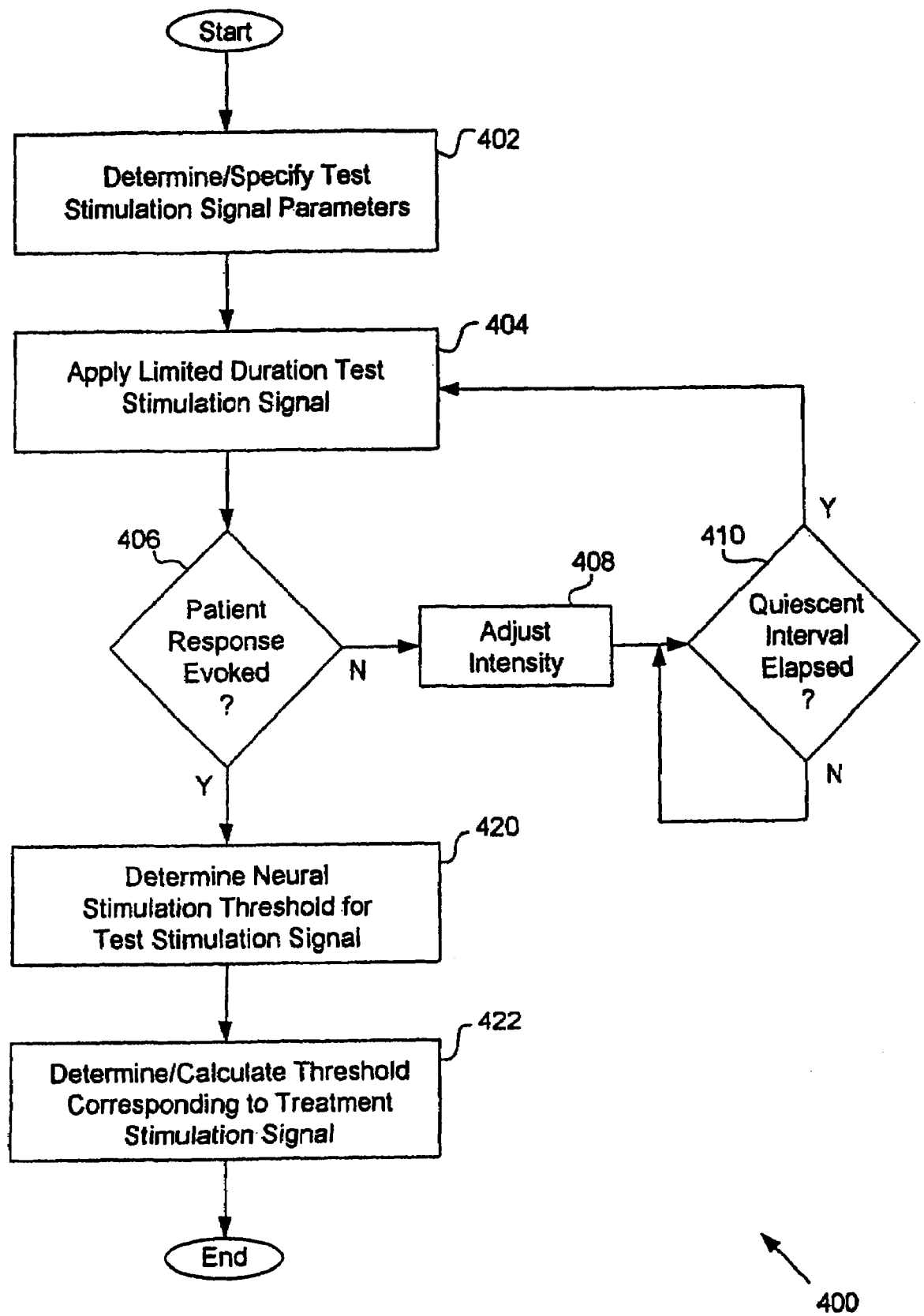
FIG. 4 is a flowchart illustrating various methods for neural stimulation threshold testing according to another embodiment of the invention.

FIG. 4 is a flowchart illustrating various methods for neural stimulation threshold testing according to another embodiment of the invention. In one embodiment, a method 400 includes a parameter determination procedure 402 that involves determining, specifying, and/or selecting test stimulation signal parameters that may reduce a likelihood of inducing collateral neural activity. In one embodiment, the pulse repetition frequency within a test stimulation signal may be higher than that within a treatment stimulation signal in order to reduce or minimize the likelihood that a significant number of neurons within a target neural population can synchronously respond to or follow the test stimulation signal. In general, a test stimulation signal needs to activate few or relatively few neurons within a target population to invoke or elicit a measurable and/or observable patient response. Thus, the pulse repetition frequency of a test stimulation signal may be higher than a neural frequency that produces a significant degradation in behavior or function (e.g., above approximately 100 Hertz), without adversely affecting the likelihood that a sufficient number of neurons can fire and evoke a patient response. In accordance with the present invention, exemplary test stimulation signal pulse repetition frequencies may be approximately 250 Hertz to approximately 400 Hertz, and in particular at the endpoints of this range.

An average amount of electrical current, charge, or energy delivered to a target neural population increases with increasing pulse repetition frequency, given constant or essentially constant test stimulation signal duration. As a result, a test stimulation signal having a higher pulse repetition frequency may be expected to elicit or evoke a measurable and/or observable patient response at a lower current level than an equivalent duration test stimulation signal having a lower pulse repetition frequency.

The method 400 may further include a signal application procedure 404 that involves application or initiation of application of (a) a first limited duration test stimulation signal having a low or very low intensity or amplitude to a target neural population within the patient 190; or (b) a next limited duration test stimulation signal having an incrementally or slightly higher intensity or amplitude than a previous test stimulation signal to the target neural population. The use of limited duration test stimulation signals may reduce or minimize the likelihood of generating prolonged neural firing responses such as afterdischarges that can increase neural excitation outside of the target population to which the test stimulation signals are applied. In general, a limited duration test stimulation signal in accordance with the present invention may be shorter than approximately 5 seconds.

The duration of a test stimulation signal applied in accordance with the present invention may depend upon a type of neural stimulation threshold currently under consideration. Thus, a limited duration test stimulation signal applied when determining one type of threshold may be shorter or longer than a limited duration test stimulation signal applied when determining another type of threshold. In general, a shorter duration test stimulation signal may deliver a lower average amount of electrical current, charge, or energy to the target neural population than a longer duration test stimulation signal given equivalent or generally equivalent pulse repetition frequencies. Hence, a shorter duration test stimulation signal may require a higher electrical current intensity, level, or amplitude to induce or evoke a given type of patient response.

With respect to determination of a movement threshold, a shorter duration test stimulation signal may evoke or induce a sharper, better defined, and hence more easily observable patient movement than a longer duration test stimulation signal. With respect to sensation threshold determination, the duration of a test stimulation signal may need to be sufficient to enable a patient 190 to accurately perceive and/or confirm perception of an induced sensation. Thus, in one embodiment, the signal application procedure 404 may apply test stimulation signals lasting at least approximately 1 second or less when the method 400 involves determination of a movement threshold; and/or apply test stimulation signals lasting approximately 3 seconds when the method 400 involves determination of a sensation threshold.

An EMG threshold may be determined in accordance with a variety of EMG measurement and/or EMG signal analysis techniques. The signal application procedure 404 may apply test stimulation signals having a duration corresponding to an EMG measurement and/or EMG signal analysis technique currently under consideration. In accordance with the signal application procedure 404, the stimulus unit 120 may issue a synchronization signal to the sensing unit 180 coincident or essentially coincident with the output of a test stimulation signal to initiate EMG signal monitoring or recording operations in a manner understood by those skilled in the art.

In one embodiment, the signal application procedure 404 may apply test stimulation signals to the patient 190 lasting approximately several milliseconds or on the order of tens of milliseconds when the sensing unit 180 is configured for EMG threshold measurement. An exemplary test stimulation signal duration corresponding to EMG threshold determination may be approximately 16 milliseconds. In such an embodiment, the signal application procedure 404 may repeat the application of a given test stimulation signal to the patient 190 multiple times to increase an EMG signal to noise ratio (i.e., to average out noise); repeated applications of the test stimulation signal may be separated by a minimum quiescent time interval as further described below. The determination of an EMG threshold using test stimulation signals having a duration on the order of milliseconds or tens of milliseconds may performed in a manner analogous or generally analogous to conventional nerve conduction studies. In another embodiment, the signal application procedure 404 may apply test stimulation signals to the patient 190 lasting approximately 1 second to 3 seconds.

In addition to the signal application procedure 404, the method 400 may include a monitoring procedure 406 that involves monitoring or observing the patient 190 and determining whether a patient behavior or reaction has been evoked or induced in response to the most recently applied test stimulation signal.

The monitoring procedure 406 may involve the sensing unit 180 and/or human perception and feedback. In the event that the method 400 involves determination of an EMG threshold, the monitoring procedure 406 may record and/or measure an EMG response during one or more portions of a test stimulation and/or throughout its entirety. The monitoring procedure 406 may additionally or alternatively perform EMG signal analysis operations to enhance MEP detectability. Such EMG signal analysis operations may include determination of changes in MEP firing or activation rates, determination of changes in MEP activation complex durations or temporal widths, root-mean-square (RMS) amplitude analysis, power spectrum analysis, correlation analysis, and/or one or more other statistical analyses.

The method 400 may also include an adjustment procedure 408 involving modification or adjustment of test stimulation signal intensity or amplitude if no patient response was evoked in association with the signal application procedure 404. In the absence of an evoked response, test stimulation signal intensity may be increased in accordance with a particular increment, for example, by 0.5 or 1.0 milliamps, or by a given percentage. The method 400 may additionally include a waiting procedure 410 involving waiting or pausing for a minimum quiescent time interval following application of a most recent test stimulation signal to the patient 190. After the minimum quiescent time interval has elapsed, the method 400 may return to the signal application procedure 404.

The use of a minimum quiescent time interval after the application of a given limited duration test stimulation signal may reduce or minimize the likelihood that neurons within the target neural population will have an increased firing susceptibility or re-excitation likelihood during application of a subsequent test stimulation signal. A minimum quiescent time interval may range from several seconds to several minutes. In an exemplary embodiment, the minimum quiescent time interval is approximately 1 minute. In an alternate embodiment, the minimum quiescent time interval may be shortened or increased depending upon a cumulative number of test stimulation signals that had been applied to the patient 190.

The method 400 may additionally include a threshold measurement procedure 420 involving measurement or determination of a neural stimulation threshold corresponding to the most recently applied test stimulation signal that evoked or induced a patient reaction or response. In one embodiment, the neural stimulation threshold corresponding to a given test stimulation signal is the electrical current level, intensity, or amplitude at which the test stimulation signal evoked or induced a particular type of patient response.

The method 400 may further include a threshold calculation procedure 422 involving calculation of a neural stimulation threshold corresponding to a treatment stimulation signal to be applied to the patient. In calculating a neural stimulation threshold corresponding to a treatment stimulation signal, the threshold calculation procedure 422 may use one or more transformation formulas and/or conversion relationships, which may be programmably stored within the stimulus unit 120. Such transformation formulas and/or conversion relationships may be based upon known parameter relationships and/or empirical data measured across a variety of test stimulation signal parameter configurations, and they may be generated using curve fitting and/or numerical modeling procedures. In one embodiment, a transformation formula appropriate for test stimulation signals and treatment stimulation signals approximately 3 seconds or longer in duration may be of the following general form:

$$I_2(f_2) = I_1(f_1) * (1 + k*(f_1^{**}q))/((1 + k*(f_2^{**}q)) \quad [1]$$

In the above equation, $I_2$ may be a peak, average, or RMS current level that defines or establishes a calculated neural stimulation threshold corresponding to the treatment stimulation signal; $f_2$ is a pulse repetition frequency associated with the treatment stimulation signal; $I_1$ is a measured neural stimulation threshold corresponding to a test stimulation signal; $f_1$ is a pulse repetition frequency corresponding to this test stimulation signal; and k and q are constants. The values of k and q may depend upon the nature of the test stimulation signals and/or the treatment stimulation signal. In an exemplary embodiment, for anodic monopolar test stimulation signals, k and q may respectively equal −0.9637 and 0.0249. For bipolar test stimulation signals, k and q may respectively equal −1.0047 and 0.0032.

The above conversion formula may scale linearly, quasi-linearly, or nonlinearly for test stimulation signal durations shorter than 3 seconds; the manner of scaling may depend upon how closely a test stimulation signal's duration approaches 3 seconds. In general, those skilled in the art will understand that additional and/or other types of transformation formulas may be defined, derived, and/or determined in accordance with particular test and/or treatment stimulation signal parameter characteristics under consideration.

A calculated neural stimulation threshold may be larger or smaller than the measured or observed neural stimulation threshold, depending upon test stimulation signal parameters and treatment stimulation signal parameters. The treatment signal may be parametrically distinct from the test stimulation signals; in particular, the treatment stimulation signal may have a different (e.g., lower) pulse repetition frequency and/or a longer (possibly continuous) duration than the test stimulation signals. The treatment stimulation signal may be delivered to the target neural population at an intensity, level, or amplitude that is a particular function or fraction of the calculated neural stimulation threshold.

Various methods for neural stimulation threshold testing in accordance with the present invention may employ additional, fewer, and/or other procedures than those described above. For example, test stimulation signals may differ from a treatment stimulation signal with respect to additional or other parameters than those described above. As another example, a procedure may include a step of verifying a calculated neural stimulation threshold by applying a treatment stimulation signal to the patient 190 at the calculated threshold, and determining whether a patient reaction occurs that is equivalent or generally equivalent to that which occurred during test stimulation signal application. A procedure may also record and store event information, data, and/or measurements obtained during test stimulation signal application. The disclosure herein provides for these and other variations, and is limited only by the following claims.

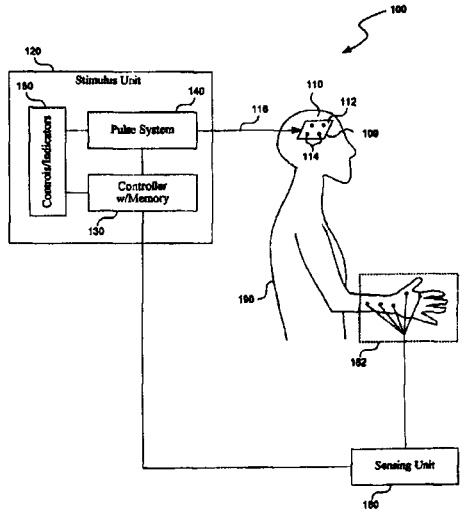

We claim:

1. A method of determining a neural stimulation threshold for a patient, comprising:
    applying a test stimulation signal to the patient;
    monitoring a neural function of the patient for a response to the test stimulation signal;
    determining a neural stimulation threshold corresponding to a lowest intensity test stimulation signal that evokes the patient response; and
    based at least in part on the neural stimulation threshold, calculating a set of parameters of a treatment stimulation signal directed toward affecting a neural activity within the patient, wherein the treatment stimulation signal differs from the test stimulation signal with respect to a plurality of parameters.

2. The method of claim 1, wherein calculating a set of parameters is performed using a transformation equation.

3. The method of claim 1, wherein the treatment stimulation signal has a different pulse repetition frequency than the test stimulation signal.

4. The method of claim 1 wherein applying a test stimulation signal to the patient includes applying a plurality of limited duration test stimulation signals to the patient.

5. The method of claim 4, wherein at least one test stimulation signal has a duration between approximately 10 milliseconds and approximately 5 seconds.

6. The method of claim 4, wherein at least one test stimulation signal has a duration of less than approximately 5 seconds.

7. The method of claim 4, wherein at least one test stimulation signal has a duration between approximately 2 seconds and approximately 3 seconds.

8. The method of claim 4, wherein at least one test stimulation signal has a duration of approximately 1 second.

9. The method of claim 4, wherein each test stimulation signal has a duration between approximately 10 milliseconds and approximately 5 seconds.

10. The method of claim 4, wherein each test stimulation signal has a duration of less than approximately 5 seconds.

11. The method of claim 4, wherein each test stimulation signal has a duration between approximately 2 seconds and approximately 3 seconds.

12. The method of claim 4, wherein each test stimulation signal has a duration of approximately 1 second.

13. The method of claim 4, wherein at least one test stimulation signal has a duration that is dependent upon a cumulative number of test stimulation signals that have been applied to the patient.

14. The method of claim 4, wherein at least one test stimulation signal has a duration that corresponds to a type of patient response under consideration.

15. The method of claim 4, wherein at least two test stimulation signals are temporally separated by a minimum time interval.

16. The method of claim 15, wherein the minimum time interval is greater than approximately 10 seconds.

17. The method of claim 15, wherein the minimum time interval is less than approximately 4 minutes.

18. The method of claim 4, wherein at least two test stimulation signals are temporally separated by a minimum time interval ranging between approximately 10 seconds and 4 minutes.

19. The method of claim 4, wherein at least two test stimulation signals are temporally separated by a minimum time interval of approximately 1 minute.

20. The method of claim 4, wherein each test stimulation signal is temporally separated by a minimum time interval.

21. The method of claim 1, wherein applying the test stimulation signals includes applying an electrical stimulation signal.

22. The method of claim 21 wherein applying an electrical stimulation signal includes applying the signal to a cortical surface of the patient's brain.

23. The method of claim 21 wherein applying an electrical stimulation signal includes applying the signal beneath a cortical surface of the patient's brain.

24. The method of claim 1, wherein the test stimulation signal has a duration between approximately 10 milliseconds and approximately 5 seconds.

25. The method of claim 1, further comprising
selecting a set of test stimulation signal parameters for the test stimulation signal that reduce a likelihood of inducing seizure activity in the patient.

26. The method of claim 25, wherein the treatment stimulation signal has a different pulse repetition frequency than the test stimulation signal.

27. The method of claim 1 wherein monitoring a neural function includes monitoring the neural function by detecting a patient behavioral response.

28. The method of claim 1 wherein applying a test stimulation signal includes applying a magnetic stimulation signal.

29. The method of claim 1 wherein calculating a set of parameters includes calculating a set of parameters of a treatment stimulation signal having a plurality of the following parameters different than corresponding parameters of the test stimulation signal: amplitude, pulse frequency, and pulse width.

30. A neuro-stimulation system comprising:
a stimulus unit configured to deliver a set of test stimulation signals to a patient; and
a controller operatively coupleable to the stimulus unit, the controller including a computer operable medium containing instructions for:
receiving an indication of a patient response to at least one of the test stimulation signals;
determining a neural stimulation threshold corresponding to a lowest intensity test stimulation signal that evokes the patient response; and
based at least in part on the neural stimulation threshold, calculating a set of parameters of a treatment stimulation signal directed toward affecting a neural activity within the patient, wherein the treatment stimulation signal differs from the test stimulation signal with respect to a plurality of parameters.

31. The neuro-stimulation system of claim 30, wherein the duration corresponding to each test stimulation signal is between approximately 10 milliseconds and approximately 5 seconds.

32. The neuro-stimulation system of claim 30, wherein the duration corresponding to each test stimulation signal is less than approximately 5 seconds.

33. The neuro-stimulation system of claim 30, wherein the duration corresponding to each test stimulation signal is between approximately 2 seconds and approximately 3 seconds.

34. The neuro-stimulation system of claim 30, wherein the minimum time interval is greater than approximately 10 seconds.

35. The neuro-stimulation system of claim 30, wherein the minimum time interval is less than approximately 4 minutes.

36. The neuro-stimulation system of claim 30, wherein the minimum time interval is greater than approximately 10 seconds and less than approximately 4 minutes.

37. The neuro-stimulation system of claim 30, wherein the minimum time interval is approximately 1 minute.

38. The neuro-stimulation system of claim 30, wherein the stimulus unit is additionally configured to deliver a set of treatment stimulation signals to the patient, at least one treatment stimulation signal directed toward affecting a neural activity within the patient.

39. The neuro-stimulation system of claim 38, wherein the treatment stimulation signal has a different frequency than a test stimulation signal.

40. The neuro-stimulation system of claim 30, wherein the stimulus unit comprises:
an electrode array configured for implantation into the patient; and
a pulse system coupled to deliver the set of test stimulation signals to the electrode array.

41. The neuro-stimulation system of claim 30, further comprising a sensing unit configured to detect a patient response to a test stimulation signal.

42. The neuro-stimulation system of claim 41, wherein the sensing unit comprises an extracranial EEG device.

43. The system of claim 41 wherein the sensing unit comprises an implanted electrode.

44. The system of claim 41 wherein the sensing unit comprises a neural function imaging device.

45. The system of claim 41 wherein the sensing unit comprises a motion detection device.

46. The system of claim 41 wherein the sensing unit is configured to detect a behavioral response.

47. The neuro-stimulation system of claim 30, wherein the computer operable medium contains instructions for causing the controller to:
use a first neural stimulation threshold corresponding to the lowest intensity test stimulation signal that evokes the patient response to determine a second neural stimulation threshold, the second neural stimulation threshold corresponding to the treatment stimulation signal directed toward affecting the neural activity within the patient.

48. The system of claim 47, wherein the treatment stimulation signal differs from the test stimulation signal with respect to a plurality of the following parameters: amplitude, pulse frequency and pulse width.

49. The system of claim 47, wherein the treatment stimulation signal has a different pulse repetition frequency than the test stimulation signal.

50. The system of claim 30, wherein the computer operable medium contains instructions for causing the controller to apply a plurality of limited duration test stimulation signals to the patient, wherein at least one test stimulation signal has a duration of less than approximately 5 seconds.

51. The system of claim 50, wherein each test stimulation signal has a duration of less than approximately 5 seconds.

52. The system of claim 50, wherein the computer operable medium contains program instructions for causing the controller to separate successive test stimulation signals by a minimum time interval.

53. The system of claim 52, wherein the minimum time interval is greater than approximately 10 seconds.

54. The system of claim 52, wherein the minimum time interval is less than approximately 4 minutes.

55. The system of claim 54, wherein the minimum time interval equals approximately 1 minute.

56. The system of claim 30 wherein the stimulus unit includes a magnetic signal generator to generate a magnetic test stimulation signal.

57. The system of claim 30 wherein the stimulus unit includes an electrical signal generator to generate an electrical test stimulation signal.

58. The system of claim 57 wherein the system further comprises a cortical surface electrode coupled to the electrical signal generator.

59. The system of claim 57 wherein the system further comprises a penetrating electrode coupled to the electrical signal generator.

* * * * *

UNITED STATES PATENT AND TRADEMARK OFFICE
CERTIFICATE OF CORRECTION

PATENT NO. : 7,620,456 B2  
APPLICATION NO. : 11/388190  
DATED : November 17, 2009  
INVENTOR(S) : Gliner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 432 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO.         : 7,620,456 B2                              Page 1 of 1
APPLICATION NO.    : 11/388190
DATED              : November 17, 2009
INVENTOR(S)        : Bradford Evan Gliner et al.

It is certified that error appears in the above-identified patent and that said Letters Patent is hereby corrected as shown below:

Insert the following claims:

--60. The method of claim 1 wherein monitoring a neural function includes monitoring the neural function via an extracranial electrode.

61. The method of claim 1 wherein monitoring a neural function includes monitoring the neural function via an implanted electrode.

62. The method of claim 1 wherein monitoring a neural function includes monitoring the neural function via a neural function imaging device.--

Signed and Sealed this
Twenty-ninth Day of November, 2011

David J. Kappos
*Director of the United States Patent and Trademark Office*

UNITED STATES PATENT AND TRADEMARK OFFICE
CERTIFICATE OF CORRECTION

PATENT NO. : 7,620,456 B2  
APPLICATION NO. : 11/388190  
DATED : November 17, 2009  
INVENTOR(S) : Bradford Evan Gliner et al.

Page 1 of 2

It is certified that error appears in the above-identified patent and that said Letters Patent is hereby corrected as shown below:

Delete the title page and substitute therefore the attached title page showing the corrected number of claims in patent.

Insert the following claims:

--60. The method of claim 1 wherein monitoring a neural function includes monitoring the neural function via an extracranial electrode.

61. The method of claim 1 wherein monitoring a neural function includes monitoring the neural function via an implanted electrode.

62. The method of claim 1 wherein monitoring a neural function includes monitoring the neural function via a neural function imaging device.--

This certificate supersedes the Certificate of Correction issued November 29, 2011.

Signed and Sealed this  
Tenth Day of January, 2012

David J. Kappos  
*Director of the United States Patent and Trademark Office*

CERTIFICATE OF CORRECTION (continued)

(12) United States Patent
Gliner et al.

(10) Patent No.: US 7,620,456 B2
(45) Date of Patent: ***Nov. 17, 2009

(54) SYSTEMS AND METHODS FOR REDUCING THE LIKELIHOOD OF INDUCING COLLATERAL NEURAL ACTIVITY DURING NEURAL STIMULATION THRESHOLD TEST PROCEDURES

(75) Inventors: Bradford Evan Gliner, Sammamish, WA (US); Kent Leyde, Redmond, WA (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 355 days.

This patent is subject to a terminal disclaimer.

(21) Appl. No.: 11/388,190

(22) Filed: Mar. 23, 2006

(65) Prior Publication Data

US 2007/0043392 A1  Feb. 22, 2007

Related U.S. Application Data

(63) Continuation of application No. 10/350,947, filed on Jan. 24, 2003, now Pat. No. 7,024,247, which is a continuation-in-part of application No. 09/978,134, filed on Oct. 15, 2001, now Pat. No. 7,305,268, which is a continuation-in-part of application No. 09/802,808, filed on Mar. 8, 2001, now Pat. No. 7,010,351.

(60) Provisional application No. 60/217,981, filed on Jul. 13, 2000.

(51) Int. Cl.
*A61N 1/00* (2006.01)

(52) U.S. Cl. .................................................... 607/45

(58) Field of Classification Search .......... 607/2, 607/45, 46, 48, 57, 63, 68 73; 600/544, 600/545; 606/129
See application file for complete search history.

(56) References Cited

U.S. PATENT DOCUMENTS 2,721,316 A  10/1955  Shaw (Continued)

FOREIGN PATENT DOCUMENTS

DE  19750043  5/1999

(Continued)

OTHER PUBLICATIONS

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

(Continued)

*Primary Examiner*—George Manuel
(74) *Attorney, Agent, or Firm*—Melissa Acosta; Peter Lando; Christopher S. L. Crawford

(57) ABSTRACT

Test procedures for determining a neural stimulation threshold of a patient. In one embodiment, the procedure includes applying a test stimulation signal to the patient and monitoring the patient for a response to the test stimulation signal. The procedure can further include determining a first neural stimulation threshold and calculating a second neural stimulation threshold. The first neural stimulation threshold corresponds to the lowest intensity test stimulation signal that evokes a patient response. The second neural stimulation threshold corresponds to a treatment stimulation signal directed toward affecting a neural activity within the patient.

62 Claims, 4 Drawing Sheets